United States Patent
Sweeney (10) Patent No.: US 10,751,436 B2
(45) Date of Patent: Aug. 25, 2020

(54) WRAPPING PROTECTOR FOR STERILIZATION TRAYS

(75) Inventor: Shaun Sweeney, Wayne, NJ (US)

(73) Assignee: Cygnus Medical, LLC, Branford, CT (US)

(*) Notice: Subject to any disclaimer, the term of this patent is extended or adjusted under 35 U.S.C. 154(b) by 1044 days.

(21) Appl. No.: 13/424,107

(22) Filed: Mar. 19, 2012

(65) Prior Publication Data
US 2013/0042576 A1 Feb. 21, 2013

Related U.S. Application Data

(60) Provisional application No. 61/454,096, filed on Mar. 18, 2011.

(51) Int. Cl.
| | | |
|---|---|---|
| B65B 11/00 | (2006.01) | |
| B65B 55/02 | (2006.01) | |
| A61L 2/28 | (2006.01) | |
| A61L 2/26 | (2006.01) | |
| A61B 50/00 | (2016.01) | |
| A61B 50/33 | (2016.01) | |
| A61B 90/00 | (2016.01) | |

(52) U.S. Cl.
CPC .............. *A61L 2/28* (2013.01); *A61B 50/00* (2016.02); *A61L 2/26* (2013.01); *A61B 50/33* (2016.02); *A61B 2050/002* (2016.02); *A61B 2090/0807* (2016.02); *A61B 2090/0813* (2016.02); *A61L 2202/182* (2013.01); *A61L 2202/24* (2013.01)

(58) Field of Classification Search
CPC ......... B65B 55/02; B65B 55/20; B65B 11/58; B65B 23/00; B65B 5/20; A61L 2/26; A61L 2/28; A61L 2202/182; A61L 2202/24; A61B 19/02; A61B 19/0271; A61B 2019/0201; A61B 2019/4838; A61B 2019/4868; A61B 50/00; A61B 50/33; A61B 2090/0813; A61B 2090/0807; A61B 2050/002
USPC ......... 53/399, 416, 419, 425, 449, 461, 472, 53/139.2, 139.7; 206/438, 439, 363, 570
See application file for complete search history.

(56) References Cited

U.S. PATENT DOCUMENTS

| | | | | |
|---|---|---|---|---|
| 4,523,679 | A | * | 6/1985 | Paikoff et al. ............... 206/370 |
| 4,639,980 | A | * | 2/1987 | Peterson ............... A61M 25/02 |
| | | | | 128/DIG. 14 |
| 4,706,839 | A | * | 11/1987 | Spence ...................... 220/315 |
| 4,868,955 | A | * | 9/1989 | Magnant ............... B65D 63/10 |
| | | | | 206/597 |

(Continued)

OTHER PUBLICATIONS

Velcro Product Guide 2010 (Bundle Ties).*

*Primary Examiner* — Thomas M Wittenschlaeger
(74) *Attorney, Agent, or Firm* — St Onge Steward Johnston & Reens LLC (57) ABSTRACT

The present invention is directed at methods of preventing damages of a sterilization wrap for surgical instruments by utilizing tray belts. The tray belts are composed of an elongate member of substantially same width and a fastening means for connecting the two ends of the member. The methods comprise the steps of placing surgical instruments inside a sterilization tray, securely the tray belts around the tray, and wrapping a sterile wrap around the tray to form a sterilization pack. The methods may further comprise securing additional tray belts around the sterilization pack.

26 Claims, 5 Drawing Sheets

(56) References Cited

U.S. PATENT DOCUMENTS

| | | | | |
|---|---|---|---|---|
| 4,876,841 | A * | 10/1989 | Jensen | B65D 71/0096 108/55.1 |
| 4,898,762 | A * | 2/1990 | Brown | A61L 2/28 156/183 |
| 5,015,251 | A * | 5/1991 | Cherubini | A44B 18/0003 128/DIG. 15 |
| 5,356,006 | A * | 10/1994 | Alpern et al. | 206/363 |
| 5,460,880 | A * | 10/1995 | Patnode | A61L 2/28 156/327 |
| 5,635,134 | A | 6/1997 | Bourne et al. | |
| 5,688,476 | A | 11/1997 | Bourne et al. | |
| 6,176,066 | B1 * | 1/2001 | Ong et al. | 53/399 |
| 6,209,723 | B1 * | 4/2001 | Fields | 206/373 |
| 6,238,623 | B1 * | 5/2001 | Amhof | A61L 2/14 116/206 |
| 6,406,764 | B2 | 6/2002 | Bayer | |
| 6,517,916 | B1 | 2/2003 | Bayer et al. | |
| 7,311,483 | B1 * | 12/2007 | Nudo | B60P 7/0869 410/41 |
| 7,780,136 | B2 | 8/2010 | Curnow et al. | |
| 8,261,963 | B2 * | 9/2012 | Gaynor | A61L 2/00 229/87.01 |
| 2002/0064478 | A1 * | 5/2002 | Davis | A61B 50/33 422/26 |
| 2004/0159568 | A1 * | 8/2004 | Rutledge | B65D 81/18 206/438 |
| 2006/0104856 | A1 * | 5/2006 | Farrell | A61L 2/07 422/1 |
| 2007/0026472 | A1 * | 2/2007 | Prokash et al. | 435/7.32 |
| 2007/0253864 | A1 * | 11/2007 | Maguire, Jr. | A61L 2/14 422/28 |
| 2008/0253947 | A2 | 10/2008 | Davis | |
| 2011/0005647 | A1 * | 1/2011 | Campfield | 150/154 |
| 2014/0048431 | A1 * | 2/2014 | Young | 206/363 |

* cited by examiner

WRAPPING PROTECTOR FOR STERILIZATION TRAYS

CROSS-REFERENCE TO RELATED APPLICATIONS

This application claims the benefit under 35 U.S.C. § 119(e) of the U.S. Provisional Patent Application Ser. No. 61/454,096, filed on Mar. 18, 2011, the contents of which are incorporated herein by reference.

FIELD OF THE INVENTION

The present invention relates generally to apparatus and methods for protecting articles during sterilization processes, and more particularly to tray belts for keeping sterilization wraps from tearing and ripping during and after a sterilization process.

BACKGROUND OF THE INVENTION

As is well known, surgical instruments used in the healthcare industry must be sterilized before and/or after each use. Sterilization, of course, frees instruments from microorganism contamination, to prevent infections and the spread of diseases among patients. All medical procedures rely upon a stringent program of sterilization.

The medical device industry has addressed the sterilization requirements in the surgical field by offering two general types of surgical instruments: reusable instruments and single use, or disposable, instruments. Reusable instruments are typically composed of stainless steel and are typically sterilized before their initial use and then cleaned and resterilized prior to each subsequent use thereof. Single use or disposable instruments, on the other hand, are often fabricated primarily from plastic materials, thereby reducing costs associated with manufacture, and are discarded after use in a single procedure.

With respect to reusable surgical instruments, e.g., forceps, graspers, dissectors, probes, hemostats, scissors and the like, sterilization and resterilization have historically been accomplished using various sterilization modalities. In a broad sense, these sterilization processes generally involve placing instruments to be sterilized in a tray, wrapping and sealing the instruments and the tray with a semi-permeable wrapping material (also called "sterilization wrap" or "sterile wrap") to form a sterilization pack or wrapped set. Next, the sterilization pack is placed in a sterilization chamber where the instruments are exposed to a sterilization medium of either steam or ethylene oxide, for sterilization. Of these two primary historical sterilization media, steam sterilization has traditionally been the overwhelmingly dominant method of sterilization in the surgical instrument field. After sterilization, the sterilization pack is cooled, dried and placed on a storage shelf or cart until the surgical instruments are needed for a surgical procedure.

One long and continuing problem encountered with sterilization packs is tears and rips of sterilization wrap prior to use of the sterilized instruments. The tears and rips may occur on both the inner and outer surfaces of the sterilization pack. The inner surface of the wrap refers to the wrap surface that is in contact with a tray. Most inner surface rips are caused by the corners and edges of the tray. This is because during repeated use, the trays may begin to oxidize and degrade, exposing sharp or rough corners and edges. The outer surface of the wrap refers to the exterior surface of a sterilization pack. The outer surface rips typically occur during shelving when a fully loaded tray, weighing up to 30 pounds each, is dragged and slid for relocation. Such dragging and sliding not only leave abrasion marks but also cause rip damages on the outer surface of the wrap by any sharp object that the pack may come in contact with. Of course, once a sterilization wrap is torn or ripped, the entire contents are deemed contaminated with bacteria and the like and, therefore, must be re-wrapped and then re-sterilized.

The problem is exacerbated by the fact that many sterilization packs become "wet packs," i.e. wrapped trays containing surgical instruments having surface moisture on the inside and/or outside of the wrapped trays during and after steam and ethylene oxide sterilization. The residual moisture makes the sterilization wrap more prone to rips and tears during sterilization processes.

One common solution to the problem focuses on rips and tears of the inner surface of the wrap caused by the tray. For example, Xodus Medical Inc. sells surgical tray corner protectors made out of regular or reticulated plastic at the dimension of 6"×6"×1⅝" for placing to the corners of a surgical tray. U.S. Pat. No. 7,780,136 discloses a surgical tray corner protector with improved drainage and air flow which comprises a support base, a side wall extending along an edge of the support base, and a plurality of apertures extending through the support base. U.S. Pat. Appl. Pub. No. 2008/0253947 discloses a foam plastic corner protector which is designed to be engaged with a surgical tray corner. While the corner protectors may guard against tears caused by the tray, they fail to prevent tears and rips on the outer surface of the wrap.

Another common practice is to provide additional layer of wrapping to reinforce the sterilization pack. This can be done by wrapping the sterilization tray with two sheets of wraps or two-ply wraps (also known as "double wrapping"), as disclosed in U.S. Pat. Nos. 5,635,134, 5,688,476, 6,406,764 and 6,517,916. However, the double wrapping practice is generally labor intensive and costly due to the increased consumption of the wrap material. Moreover, the double wrapping practice does not resolve the damages to the inner surface of the wrap.

What is desired, therefore, is a wrapping protector for sterilization trays which can be used to prevent tears and rips on the outer surface of the wrap. Preferably the wrapping protector can also be used directly on the tray so as to prevent tears and rips on the inner surface of the wrap. More preferably, the wrapping protector can be easily applied to a sterilization tray or a sterilization pack and also cost effective.

SUMMARY OF THE INVENTION

The prevent invention is intended to obviate many problems associated with tears and rips in sterilization wraps during sterilization processes. Rather than employing corner protectors for corner relief or relying on the double wrapping practice, as have been done in the past, the present invention employs tray belts to prevent damages to the wrap in the sterilization processes. The tray belts may be used on the outside of the wrapped set as well as between the tray and the wrap.

When used on the outside of the wrapped set, the tray belt prevents abrasion marks caused by dragging and sliding the tray as well as rip damages caused by many sharp objects that the tray may come in contact with. Consequently, both the outer surface of the wrap and the instruments contained therein are well-protected. The tray belt used outside the wrap may optionally contain adhesives bounded on one surface of the member (e.g. conventional adhesive tapes). Such adhesives may be used as a fastening means and a sterilization indicator if they change colors upon sterilization.

When used between the tray and the wrap, the tray belt protects the inner surface of the wrap against the tray edges and protruding tray feet and latches. The tray and the tray belt are then wrapped with a sterilization wrap to form a sterilization pack. The sterilization pack may further be protected by additional tray belts positioned outside the sterilization pack.

In both applications, it has been found that positioning the tray belts near or approximately on the corner of the wrapped set or the tray provides excellent results because most damages occur on or near the corners. But the tray belts may be also positioned anywhere in between any two parallel tray edges. Multiple tray belts, either substantially parallel to one another or substantially perpendicular to one another, can be used for optimal protection.

As exemplified in the Figures and described in detail herein, the tray belts have an elongate member of substantially same width and a fastening means for connecting two ends of the member and for tightly securing the tray belt on the tray or the wrapped set. The fastening means can be provided by any interlocking geometric shaped materials, although a hook-and-loop fastener is one preferred fastening means due to its convenience to use and low cost.

The tray belts may employ any reusable or disposable material that provides flexibility, strength, properties suitable for sterilization, and backing support for the fastening means. Suitable reusable materials for this invention include heavy duty cloth, linen or other woven materials. Suitable disposable materials for this invention include nonwoven materials made from either or both natural and synthetic fibers such as cellulose, rayon, nylon, polyesters, and polyolefins.

In accordance with the present invention, methods of preventing damages to a sterilization wrap during the sterilization processes may comprise the steps of placing instruments inside a tray, securing one or more tray belts around the tray, wrapping a sterilization wrap around the tray to form a sterilization pack, and securing one or more tray belts around the sterilization pack.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF THE INVENTION

The present invention provides methods of preventing damages to a sterilization wrap for surgical instruments by securing tray belts on the tray and/or outside the sterilization wrap.

Figure 1:
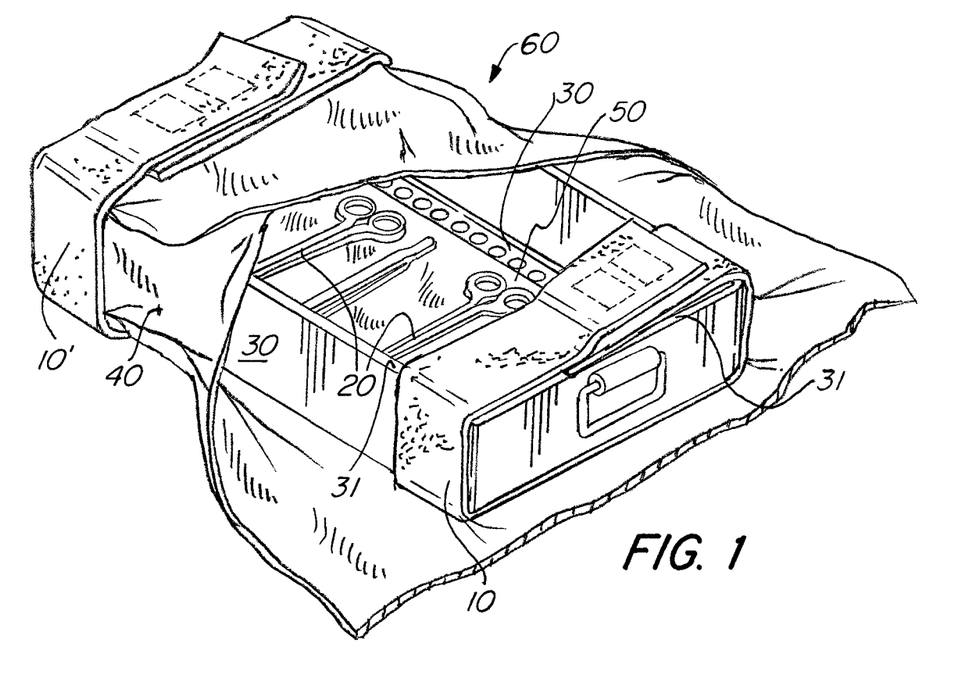
FIG. 1 is a perspective view of a sterilization system having tray belts placed over a sterilization tray and over a sterilization pack according to the present invention.

FIG. 1 shows a first embodiment of the invention in which both the inner and outer surfaces of the sterilization pack 60 have been protected with tray belts 10, 10'. A tray belt 10 is wrapped around a tray 30 to prevent a wrap 40 from contacting part of tray edges 31. As such, the tray belt 10 serves to shield the inner surface of the wrap 40 from damages caused by protruding tray feet and latches of the tray 30. A tray belt 10' is secured around the wrap 40 to tightly reinforce the wrapping around the edges and other parts of the sterilization pack 60. Because the tray belt 10' is more durable against sharps and abrasion compared to the wrap 40, the sterilization pack 60 is less prone to abrasion marks and rip damages caused by many sharp objects that the tray 30 may come in contact with during shelving and sterilization.

Figure 2:
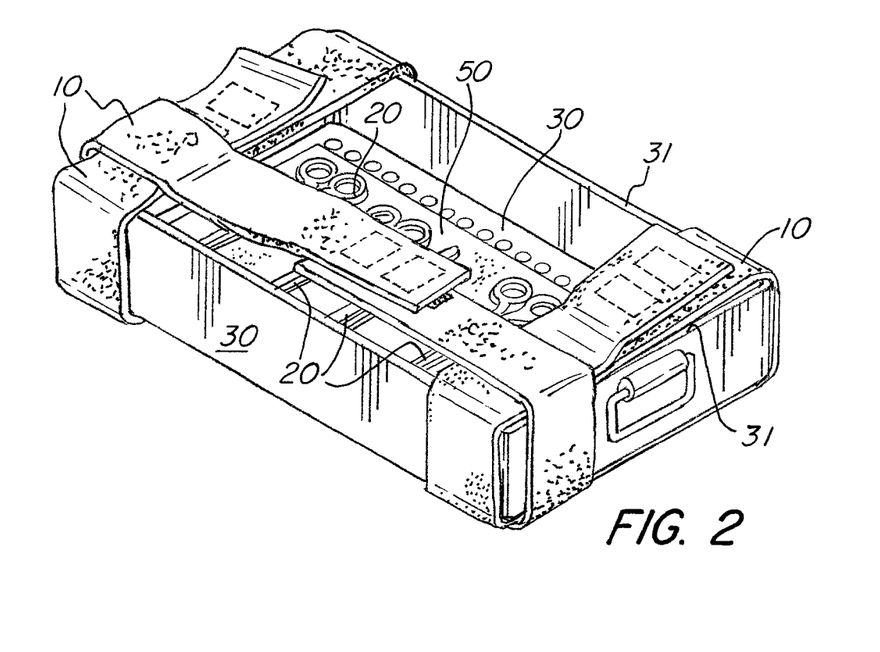
FIG. 2 is a perspective view of a sterilization system having tray belts placed over a sterilization tray according to the present invention.

FIG. 2 shows a second embodiment of the invention in which only the inner surface of the sterilization pack has been protected with tray belts 10. In doing so, the tray belts 10 are placed around a tray 30 and form a separation between the edges 31 of the tray 30 and the inner surface of a wrap 40.

Figure 3:
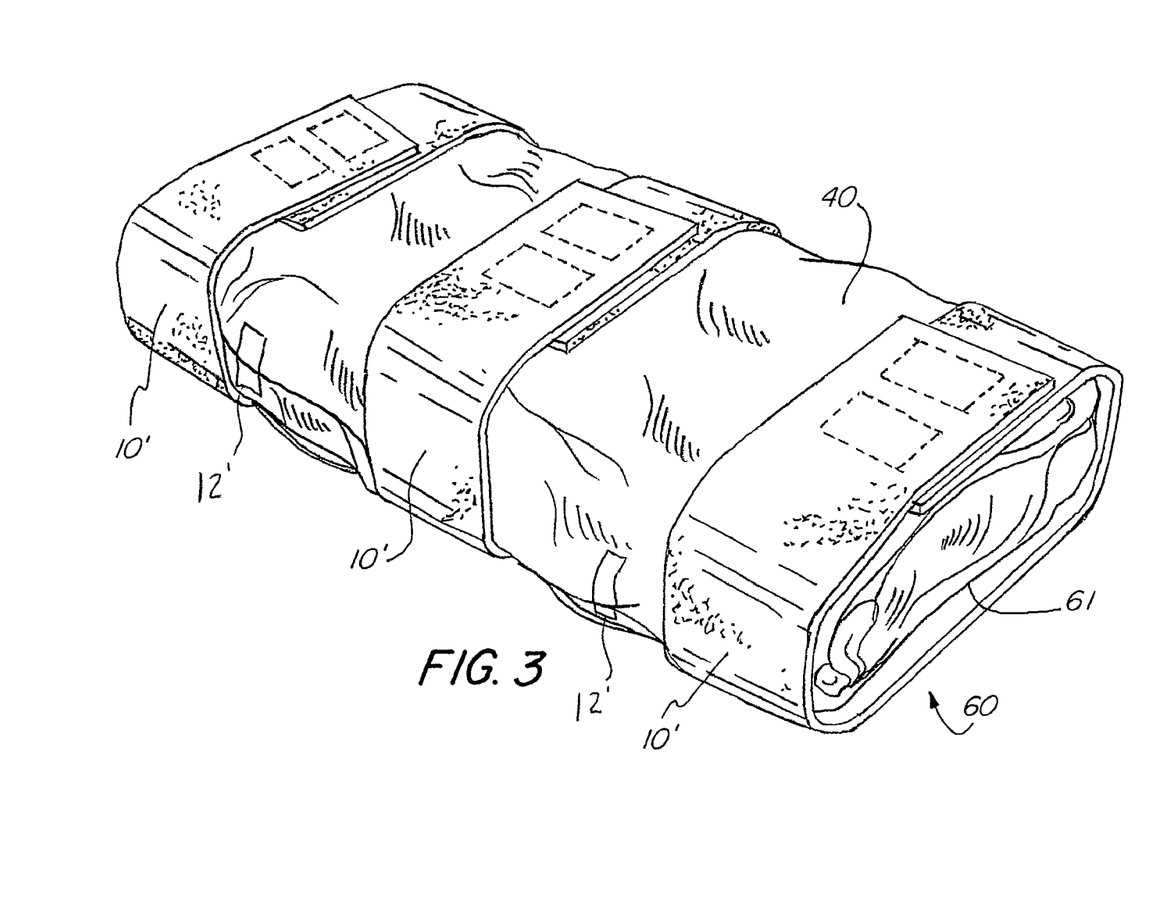
FIG. 3 is a top view of a sterilization system having tray belts placed over a sterilization pack according to the present invention.

FIG. 3 shows a third embodiment of the invention in which only the outer surface of a sterilization pack has been protected by securing tray belts 10' around the outer inner surface of a sterilization pack 60.

In all these embodiments, the tray belts 10, 10' are substantially parallel to one edge 31 of the tray 30 or to one edge 61 of the sterilization pack 60. More than one tray belts can be used on the tray or on the sterilization pack for better protection. The tray belts 10, 10' may be positioned substantially parallel to one another. Alternatively they may also be positioned substantially perpendicular to one another. It has been found that positioning the tray belts 10, 10' near or approximately on the corner of the sterilization pack 60 or the tray 30 provides excellent results because most damages to the wraps 40 occur on or near the corner.

Figures 4A, 4B:
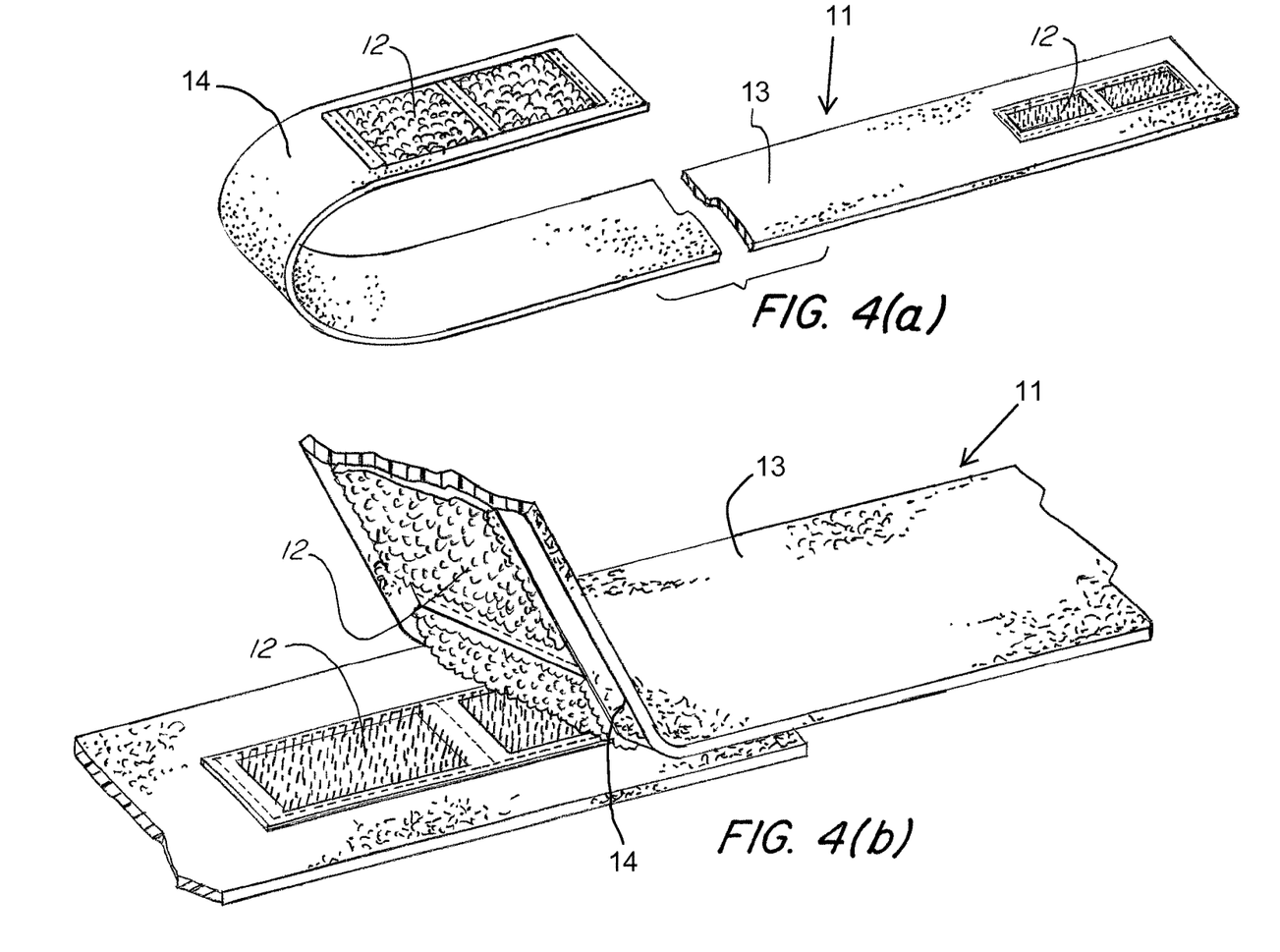
FIG. 4(a) is a top view of an exemplary embodiment of a tray belt according to the present invention.
FIG. 4(b) is a perspective view of a tray belt in which the two ends of the tray belt are connected by a hook-and-loop fastener according to the present invention.

FIGS. 4(a) and 4(b) illustrate an exemplary embodiment of the tray belts 10, 10' according to the present invention. In general, the tray belts 10 comprise an elongate member 11 having a width and a length and a fastening means 12 for connecting two ends of the member 11. The width of the member 11 is substantially the same over the member 11. The member 11 includes a first surface 13 and a second surface 14 which is on the opposite side the first surface 13.

Because the tray belts 10 are used for providing backing to the fastening means 12 and for wrapping a tray 30 in a sterilization process, it requires the tray belts 10 be made of a material that provides flexibility, strength, and properties suitable for sterilization and for backing support. In order to prevent abrasion and puncture damages to the outer surface of the wrap 40 during dragging and sliding of the tray, it additionally requires the tray belts 10 be made of a material that is durable against abrasion and puncturing. The tray belts 10 can be made from reusable and disposable materials. Suitable reusable materials for this invention include heavy duty cloth, linen or other woven materials. Suitable disposable materials for this invention include nonwoven materials made from either or both natural and synthetic fibers such as cellulose, rayon, nylon, polyesters, and polyolefins.

The fastening means 12 can be provided by interlocking geometric shaped materials, such as hook, loops, bulbs, mushrooms, arrowheads, balls on stems, male and female mating components, clips, buckles, snaps, buttons, or the like.

In one aspect of the present invention, the fastening means is provided by a hook-and-loop fastener which is securely attached to the surfaces of the member, as illustrated in FIGS. 4(a) and 4(b). A hook-and-loop fastener is a preferred fastening means because they are easy to use and readily available. The dimensions of hooks and loops and their relative positions on the surfaces may vary. While the hooks and loops may have substantially the same dimensions as those of the first and second surfaces 13 and 14, it may be economical to have hooks and loops of smaller dimensions than the surfaces 13 and 14, as shown in FIG. 4(a). The hooks may appear on the first surface 12 near one end of the member 11, and the loops may appear on the second surface 13 near the other end of the member 11, leaving most part of the surfaces free of hooks and loops. This configuration allows the loop and the hook to latch on one other after the member 11 is wrapped around on the tray 30 or the wrap 40 without twisting the surfaces of the member 11. Regardless the dimensions and positions of the hooks and loops for each tray belt, there should be adequate overlaps of the hooks and loops in order to provide sufficient level of fastening strength to hold the pack during sterilization processes and allow for adjusting the tightness of the belt on the tray or the wrapped pack.

The hooks and loops can be made of nylon, polyester, Teflon, or other materials as known in the art. One skilled in the art will recognize that the shape, density and polymer composition of the hooks and loops may be selected to obtain the desired level of fastening between the hooks and loops. Commercial Velcro® brand and Duragrip™ brand hook and loop fasteners that are compatible with sterilization processes can be used for the present invention.

In some embodiments, the fastening means is provided by adhesives bounded on one surface of the member (e.g. conventional adhesive tapes). Such adhesives not only may function as a fastening means to the tray belt, they may also serve as a sterilization indicator if they are designed to change colors upon sterilization. In practice, this type of tray belts may be used in conjunction with the tray belts having hook-and-loop fasteners.

Figure 5:
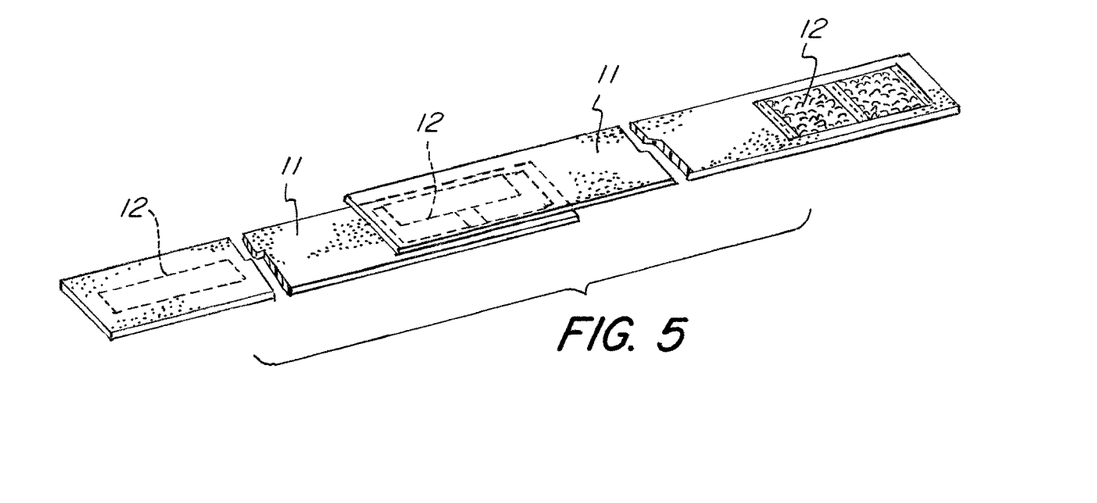
FIG. 5 is a perspective view of two tray belts connected to one another to extend the length of the tray belts according to the present invention.

The tray belts 10, 10' may come in various lengths, which is defined by the distance between the two ends of the member 11. In the event that one tray belt is too short for wrapping, two or more tray belts may be connected with one and another to provide a single long tray belt, as depicted in FIG. 5.

Figure 6:
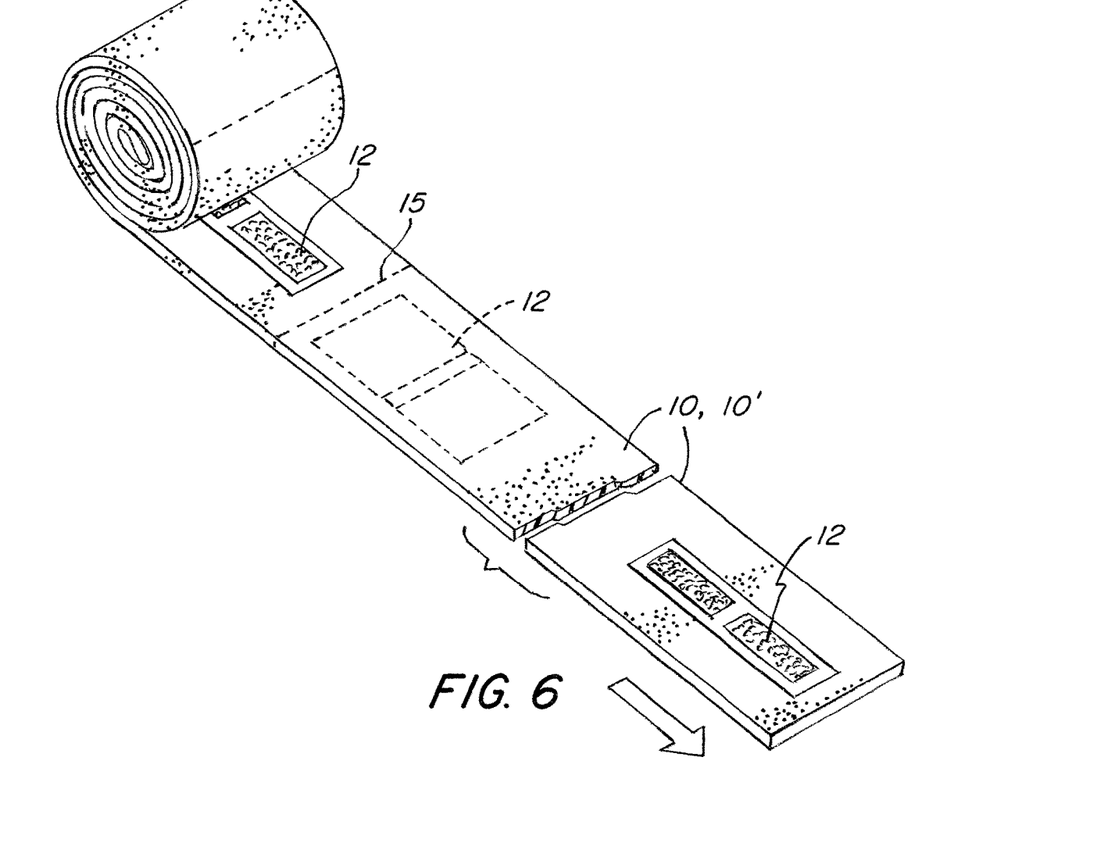
FIG. 6 is an alternate perspective view of tray belts according to the present invention.

The tray belts 10, 10' made of hook and loop fasteners may be supplied in continuous roll form so that one may cut the belt to obtain desired length, as depicted in FIG. 6. When provided as a continuous roll, a length of 35 to 40 feet is preferred. In one embodiment, a roll of the tray belt is about 4 inch wide and about 36 feet long. One skilled in the art will recognize that tray belt rolls in different width and length can be used.

The tray belts 10, 10' may, optionally, contain perforations 15 along the width of the belt 10, 10'. The perforations 15 allow the tray belt 10, 10' to be torn off a continuous roll, as depicted in FIG. 6. The perforations 15 may be placed at any suitable interval so that the length of the belt can be chosen to accommodate sterilization trays of different sizes.

In one aspect, a method of preventing damages to a sterilization wrap during the sterilization processes according to the present invention comprises the steps of providing a tray 30, placing instruments 20 inside the tray 30, securing one or more tray belts 10 around the tray 30, wrapping a sterilization wrap 40 around the tray 30 to form a sterilization pack 60.

The method may optionally include a step of providing a tray liner 50 inside the tray 30 for receiving the instruments 20 before the step of placing the instruments 20 inside the tray 30. The tray liner 50 may function as a cushion to the instruments 20. The tray liner 50 may be formed of a single material, such as open or closed cell foam or a cellulose based material. It may also be formed of two-ply liners comprised of a foam layer and a backing layer made of plastic or cloth.

The types of instruments 20 that may benefit from sterilization method disclosed herein include all conventional surgical instruments composed of stainless steel. Determinations as to the types of surgical instruments to be placed on the tray 30, the numbers/weights of such surgical instruments, sterilization cycles, and the like, are made according to conventional sterilization criteria.

The tray 30 can be secured with one or more tray belts 10 by first positioning the tray belt 10 around the tray 30 wherein the tray belt 10 is substantially parallel to one edge 31 of the tray 30, followed by fastening the two ends of the tray belt 10 to tightly secure it on the tray 30.

The tray 30 and the tray belts 10 are then advantageously wrapped in a conventional sterilization wrap 40. The sterilization wrap 40 should be permeable to sterilizing gases yet impermeable to potentially contaminating microorganisms. It should also have good drapeability and makes crisp folds and tucks. One commonly used wrap is central supply room (CSR) which is typically formed of non-woven polypropylene. The loose ends of the sterilization wrap that remain after making the final fold can be secured with a piece of adhesive tape 12' (see FIG. 3). In addition to holding the loose ends of the sterilization wrap, the adhesive tape is often designed to change color upon being exposed to sterilization conditions. As such the adhesive tape acts as an external indicator as to whether or not a sterilization pack has been subjected to sterilization conditions.

Once wrapped in the sterilization wrap 40, the resulting sterilization pack 60 is ready to be placed in a sterilization unit for a sufficient time for sterilization of the surgical instruments 20. At the conclusion of the sterilization cycle, the sterilization pack 60 is typically removed from the sterilization unit (not pictured) for cooling and storage, and the sterilized instruments 20 are, in due course, removed from the tray and made ready for subsequent surgical procedures.

In another aspect, a method of preventing damages to a sterilization wrap during the sterilization processes according to the present invention may comprise the step of securing one or more tray belts 10' around a conventional sterilization pack 60. By the word "conventional," it refers to the sterilization pack 60 which does not have any tray belt 10 wrapped around a tray 30. The method comprises the steps of providing a tray 30, optionally providing a tray liner 50, placing instruments 20 inside the tray 30, wrapping a sterilization wrap 40 around the tray 30 to form a conventional sterilization pack 60, and securing one or more tray belts 10' around the conventional sterilization pack 60.

The step of securing the tray belt 10' around the sterilization pack 60 includes positioning the tray belt 10' around the sterilization pack 60 wherein the tray belt 10' is substantial parallel to one edge 61 of the sterilization pack 60, followed by fastening the two ends of the tray belt 10' to tightly secure it on the sterilization pack 60.

Figure 7:
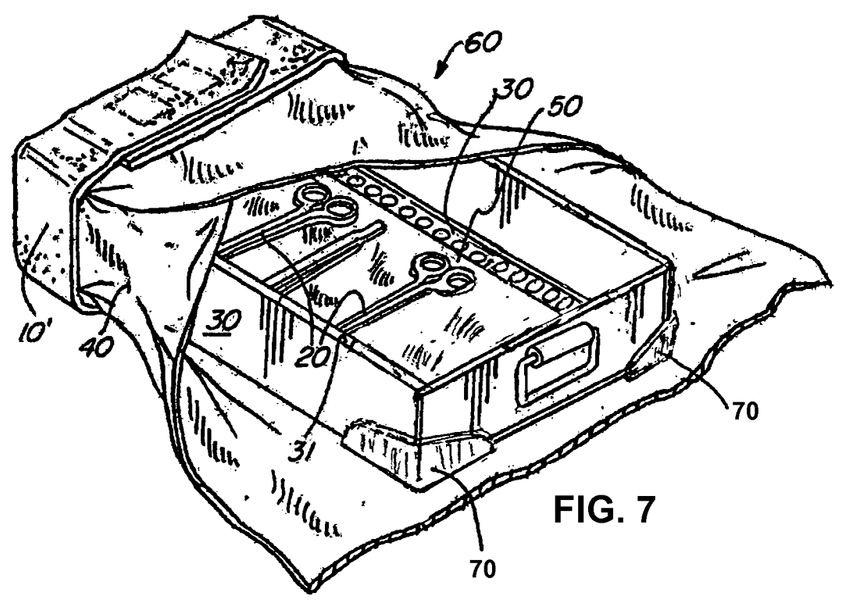
FIG. 7 is a perspective view of a sterilization system placing corner protectors on a sterilization tray before wrapping the tray with a sterilization wrap according to the present invention.

The method may further comprise the step of providing corner relief to the tray 30 by using corner protectors 70 before wrapping the tray 30 with a sterilization wrap 40 to form the sterilization pack 60, as shown in FIG. 7. The corner protectors can be those described in the Background of the application, i.e., the surgical corner protectors sold by Medical Inc., or those disclosed in U.S. Pat. No. 7,780,136 or U.S. Pat. Appl. Pub. No. 2008/0253947.

In a further aspect, a method of preventing damages to a sterilization wrap during the sterilization processes according to the present invention placing tray belts 10, 10' on both a tray and outside of a sterilization pack 60 for optimal protection. The method comprises the steps of providing a tray 30, optionally providing a tray liner 50, placing instruments 20 inside the tray 30, securing one or more tray belts 10 around the tray 30, wrapping a sterilization wrap 40 around the tray 30 to form a sterilization pack 60, and securing one or more tray belts 10' around the sterilization pack 60.

The principles, preferred embodiments and modes of operation of the presently disclosed tray belts and methods of sterilizing surgical instruments using the tray belts have been described in the foregoing specification. The presently disclosed tray belts and methods of sterilization, however, are not to be construed as limited to the particular embodiments shown as these embodiments are regarded as illustrious rather than restrictive. Moreover, variations and changes may be made by those skilled in the art without departing from the spirit of the presently disclosed tray belts, and methods of sterilization.

What is claimed is:

1. A method of preventing damage to a sterilization pack for surgical instruments, comprising the steps of:
    providing a tray, said tray having a width, a length, and a depth;
    placing said surgical instruments inside said tray;
    wrapping at least one inside tray belt around said tray, said at least one inside tray belt being an elongate member having a width and a length;
    securing said at least one inside tray belt around said tray by fastening two ends of the elongate member to each other;
    wrapping a sterile wrap, in a form of a sheet, around said tray and said at least one inside tray belt to form said sterilization pack; and
    wrapping two or more outside tray belts around said sterile wrap, said two or more outside tray belts each being an elongate member having a width and a length;
    securing said two or more outside tray belts and loose ends of said sterile wrap with fasteners, the fasteners including adhesive that changes color upon being exposed to sterilization conditions.

2. The method of claim 1, wherein said at least one inside tray belt extends along and adjacent to a lengthwise edge of said tray.

3. The method of claim 1, wherein at least one of said two or more outside tray belts extends along and adjacent to an edge of said sterilization pack.

4. The method of claim 1, wherein said at least one inside tray belt and said two or more outside tray belts are made of heavy duty cloth, linen, cellulose, rayon, nylon, polyester, or polyolefin.

5. The method of claim 1, wherein the fasteners further include hook-and-loop fasteners.

6. The method of claim 5, wherein said hook-and-loop fasteners are made of nylon, polyester or Teflon.

7. The method of claim 1, wherein said width of said elongated member of said at least one inside tray belt and of said two or more outside tray belts is about 4 inches.

8. The method of claim 1, wherein said at least one inside tray belt and said two or more outside tray belts are provided from a continuous roll of tray belt material.

9. The method of claim 8, wherein said continuous roll includes perforations at a plurality of intervals along the tray belt material.

10. The method of claim 1, further comprising the step of providing a tray liner inside said tray for receiving said surgical instruments.

11. The method of claim 1, wherein said at least one inside tray belt extends adjacent to a corner of said tray, the corner being where three sides of said tray meet.

12. The method of claim 1, wherein a first one of said two or more outside tray belts extends along and adjacent to a first edge of said sterilization pack and a second one of said two or more outside tray belts extends along and adjacent to a second edge of said sterilization pack.

13. A method of preventing damage of a sterilization pack for surgical instruments, comprising the steps of:
    providing a tray, said tray having a width, a length, and a depth;
    placing said surgical instruments inside said tray;
    wrapping a sterile wrap, in a form of a sheet, around said tray to form said sterilization pack;
    providing two or more tray belts, each of said two or more tray belts being an elongate member with two ends, said two or more tray belts comprised of a material permeable to sterilizing gases; and
    securing said two or more tray belts around said sterilization pack by fastening said two ends of said member;
    wherein a first one of said two or more tray belts extends along and adjacent to a first edge of said sterilization pack and a second one of said two or more tray belts extends along and adjacent to a second edge of said sterilization pack,
    wherein each of said two or more tray belts also extends adjacent to at least one corner of said sterilization pack, the at least one corners being where three sides of said sterilization pack meet.

14. The method of claim 13, further comprises the step of providing corner protectors to said tray prior to the step of wrapping said sterile wrap around said tray.

15. The method of claim 13, further comprising the step of wrapping at least one inside tray belt around said tray prior to wrapping said tray in the sterile wrap, the at least one inside tray belt extending along and adjacent to a lengthwise edge of said tray.

16. The method of claim 13, further comprising the step of securing loose ends of the sterile wrap with adhesive tape that changes color upon being exposed to sterilization conditions.

17. The method of claim 13, further comprising the step of providing a tray liner inside said tray for receiving said surgical instruments.

18. The method of claim 13, wherein said fastener includes an adhesive designed to change color upon being exposed to sterilization conditions.

19. The method of claim 13, wherein said two or more tray belts are provided from a continuous roll of tray belt material, said continuous roll including perforations at a plurality of intervals along the tray belt material.

20. The method of claim 13, wherein the step of providing two or more tray belts includes providing two or more tray belts comprised of a cellulose material.

21. The method of claim 13, the step of providing two or more tray belts includes providing two or more tray belts comprised of a material that is permeable to ethylene oxide and steam.

22. An apparatus for sterilization, comprising:
a sterilization tray, said tray having a width, a length, and a depth;
surgical instruments inside said sterilization tray;
a sterile wrap, in a form of a sheet, wrapped around and enclosing said sterilization tray to form a sterilization pack; and
two or more tray belts, each of said two or more tray belts being an elongate member with two ends and comprised of a material permeable to sterilizing gases, secured around said sterilization pack outside of said sterile wrap by fastening the two ends of each of said two or more outside tray belts;
wherein a first one of said two or more tray belts extends along and adjacent to a first edge of said sterilization pack and a second one of said two or more tray belts extends along and adjacent to a second edge of said sterilization pack, and
wherein said two or more outside tray belts each extend adjacent to corners of said sterilization pack, the corners of said sterilization pack being where three sides of said sterilization pack meet.

23. The apparatus according to claim 22, further comprising a continuous roll of tray belt material, wherein said two or more tray belts are provided from the continuous roll of tray belt material.

24. The apparatus according to claim 22, wherein loose ends of said sterile wrap are secured with an adhesive tape, wherein the adhesive tape changes color upon being exposed to sterilization conditions.

25. The apparatus of claim 22, wherein the material permeable to sterilizing gases is a cellulose material.

26. The apparatus of claim 22, wherein the sterilizing gases to which the material is permeable include ethylene oxide and steam.

* * * * *